United States Patent
Malle et al.

(10) Patent No.: US 6,322,775 B1
(45) Date of Patent: Nov. 27, 2001

(54) COSMETIC COMPOSITIONS CONTAINING PYRAZOLIN-4,5-DIONES, NOVEL PYRAZOLIN-4,5-DIONES, PREPARATION METHODS THEREFOR AND USES THEREOF

(75) Inventors: Gérard Malle, Villiers sur Morin; Laurent Vidal, Paris, both of (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/155,213

(22) PCT Filed: Mar. 12, 1997

(86) PCT No.: PCT/FR97/00438

§ 371 Date: Jan. 6, 1999

§ 102(e) Date: Jan. 6, 1999

(87) PCT Pub. No.: WO97/35842

PCT Pub. Date: Oct. 2, 1997

(30) Foreign Application Priority Data

Mar. 22, 1996 (FR) .................................................. 96 03625

(51) Int. Cl.⁷ .............................. A61K 7/42; A61K 7/06; A61K 31/415; C07D 231/02; C07D 231/30
(52) U.S. Cl. .......................... 424/59; 424/70.1; 514/404; 514/406; 514/407; 548/366.4; 548/369.4; 548/371.1
(58) Field of Search .................... 424/59, 70.1; 514/404, 514/407, 406; 548/366.4, 369.4, 371.1

(56) References Cited

U.S. PATENT DOCUMENTS

| | | |
|---|---|---|
| 3,061,432 | 10/1962 | Menzel et al. . |
| 3,227,554 | 1/1966 | Barr et al. . |
| 3,419,391 | 12/1968 | Young . |
| 3,725,067 | 4/1973 | Bailey et al. . |
| 3,820,948 | 6/1974 | Berth . |
| 3,926,631 | 12/1975 | Arai et al. . |
| 4,128,425 | 12/1978 | Greenwald . |
| 4,293,543 | 10/1981 | Cotte et al. . |
| 4,500,630 | 2/1985 | Sato et al. . |
| 5,256,526 | 10/1993 | Suzuki et al. . |
| 5,441,863 | 8/1995 | Tang et al. . |
| 5,457,210 | 10/1995 | Kim et al. . |

FOREIGN PATENT DOCUMENTS

| | | |
|---|---|---|
| 2 160 317 | 6/1973 | (DE) . |
| 2 359 999 | 6/1975 | (DE) . |
| 3 731 395 | 4/1989 | (DE) . |
| 3 843 892 | 6/1990 | (DE) . |
| 4 009 097 | 9/1991 | (DE) . |
| 4 133 957 | 4/1993 | (DE) . |
| 0 030 680 | 6/1981 | (EP) . |
| 0 119 860 | 9/1984 | (EP) . |
| 0 285 274 | 10/1988 | (EP) . |
| 0 304 001 | 2/1989 | (EP) . |
| 0 309 652 | 4/1989 | (EP) . |
| 0 320 764 | 6/1989 | (EP) . |
| 0 456 226 | 11/1991 | (EP) . |
| 0 488 248 | 6/1992 | (EP) . |
| 0 488 909 | 6/1992 | (EP) . |
| 0 518 238 | 12/1992 | (EP) . |
| 0 547 864 | 6/1993 | (EP) . |
| 0 557 851 | 9/1993 | (EP) . |
| 0 578 248 | 1/1994 | (EP) . |
| 0 591 103 | 4/1994 | (EP) . |
| 1 564 999 | 4/1969 | (FR) . |
| 2 075 583 | 10/1971 | (FR) . |
| 2 466 492 | 4/1981 | (FR) . |
| 2 486 913 | 3/1987 | (FR) . |
| 1 026 978 | 3/1963 | (GB) . |
| 1 153 196 | 8/1966 | (GB) . |
| 1 458 377 | 9/1974 | (GB) . |
| 58 42045 | 3/1983 | (JP) . |
| 59 99437 | 6/1984 | (JP) . |
| 59 162548 | 9/1984 | (JP) . |
| 59 171956 | 9/1984 | (JP) . |
| 60 33552 | 2/1985 | (JP) . |
| 60 43659 | 3/1985 | (JP) . |
| 60 172982 | 9/1985 | (JP) . |
| 60 190779 | 9/1985 | (JP) . |
| 62 79337 | 12/1987 | (JP) . |
| 63 169571 | 7/1988 | (JP) . |
| 62 36011 | 8/1994 | (JP) . |
| 70 36159 | 2/1995 | (JP) . |
| 70 84348 | 3/1995 | (JP) . |
| 70 92632 | 4/1995 | (JP) . |
| WO 92/04349 | 3/1992 | (WO) . |
| WO 92/04883 | 4/1992 | (WO) . |
| WO 94/04130 | 3/1994 | (WO) . |
| WO 94/08959 | 4/1994 | (WO) . |
| WO 94/08969 | 4/1994 | (WO) . |
| WO 94/89970 | 4/1994 | (WO) . |

OTHER PUBLICATIONS

CA102:80260;Koraiem,Al Mohmoud,JPrak.Chem '84,326, 811;Apocyanine dyes . . . , May 1984.*

Webster's II New Riverside University Dictionary:(1994), "Definition of Cosmetic".*

R. Stollé , "Ueber die Ueberführung der secundären Säurehydrazide in Derivate des Furodiazols, Pyrrodiazols und Thiodiazols", Chemischen Gesellschaft, pp. 797–798, 1899.

Hans Beyer et al., "Über die Pyrazolbildung aus α–Chlor–acetessigester und Thiocarbohydazid", Chemische Berichte, pp. 2550–2555, 1956.

H. Wilde et al., Synthese von 4H–Pyrazolo[1,5–a]benzimidazolen, Journal Für Praktische Chemie, pp. 829–836, 1984.

(List continued on next page.)

*Primary Examiner*—Mukund J. Shah
*Assistant Examiner*—Sudhaker B. Patel
(74) *Attorney, Agent, or Firm*—Finnegan, Henderson, Farabow, Garrett & Dunner, L.L.P.

(57) ABSTRACT

The present invention relates to novel cosmetic compositions, in particular for coloring the skin and/or the hair, comprising, in a cosmetically acceptable support, at least one 4,5-pyrazolinedione. The invention also relates to novel 4,5-pyrazolinediones, to processes for their preparation and to their uses in the cosmetics field.

12 Claims, No Drawings

OTHER PUBLICATIONS

Lidia Wyzgowska et al., "O Reakcjach Trikarboetoksymetanu VIII", Acta Poloniae Pharmaceutica, pp. 83–88, 1982.
E. Hannig et al., "Zur Kenntnis des 4–aminierten Phenylbutazons", Die Pharmazie, pp. 231, 1980.
Giuliana Cardillo et al., "Su due constituenti minori della Kamala", Gazetta Chimica Italiana, pp. 725–734, 1965.
Thomas Kauffmann et al., Synthese von Amidrazonon aus Nitrilen und Natriumhydrazid, pp. 3436–3443, 1964.
von Helmut Dorn et al., "Synthese und Methylierung von 1$H$–Pyrazolo[3,4–b]pyrazinen, einer neuen Klasse von Purin–Antagonisten", Annalen der Chemie, pp. 118–123, 1968.
von Helmut Dorn et al., "Über die elektrophile Substitution von 3(5)–Amino–pyrazol", Annalen der Chemie, pp. 141–146, 1967.
Mohamed Helmi Elnagdi et al., "Studies on 3,5–pyrazolidinediones. IV. Addition of 4–Arylazo–3,5–pyrazolidinediones to Ethyl Acrylate", Bulletin of Them Chemical Society of Japan, vol. 46, pp. 1830–1833, 1973.
Günther Ege et al., "A Simple Synthesis of 3(5)–Aminopyrazole", Angew. Chem. internat. Edit, vol. 13, No. 3, pp. 206–207, 1974.
Kazumasa Takahashi eta al., "Syntheses of 3(5)–Substituted–4– ($N$ –methylanilino)–5(3)–aminopyrazoles by Reaction of β–Hydroxy–α–cyano–enamines with Hydrazines", Journal of Synthetic Organic Chemistry, No. 8, pp. 794–796, 1985.
Chiara B. Vincentini et al., "Pyrazolo[3,4–$d$][1,2,3] Triazole–1–carboxamides and 5–Alkylaminopyrazolo [3,4–$d$]oxazoles: Synthesis and Evaluation of the in Vitro Antifungal Activity", I1 Farmaco, vo. 47, No. 7, 8, pp. 1021–1034, 1992.

Edward C. Taylor et al., "The Reaction of Malononitrile with Substituted Hydrazines: New Routes to 4–Aminopyrazolo[3,4–d]pyrimidines", Journal of the merican Chemical Society, vol. 81, No. 10, pp. 2456–2464, 1959.
C.B. Vincentini et al., "A New Fused Heterocyclic System: 6$H$–Pyrazolo[3,4–c][1,2,5]thiadizine 2,2–Dioxide", Journal of Heterocyclic Chemistry, vol. 26, No. 3, pp. 797–803, 1989.
E.J. Browne et al., "Triazoles. Part VII. Syntheses of Substituted 1,2,4–Triazoles", Journal of The Chemical Society, pp. 5149–5152, 1962.
Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, 1990.
Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, vol. 109, No. 9, pp. 2711–2717, 1987.
H. Koopman, "Investigations on Herbicides IV, The synthesis of 2,6–dichlorobenzonitrile", Recueil, vol. 80, No. 9–10, pp. 1075–1083, 1961.
Joseph Bailey, "Synthesis of 1$H$–Pyrazolo[3,2–$c$]–$s$–Triazoles and Derived Azamethine Dyes", Journal of the Chemical Society, pp. 2047–2052, 1977.
Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Jounral f. prakt. chemie, Band 320, heft 4, pp. 533–538, 1978.

* cited by examiner

COSMETIC COMPOSITIONS CONTAINING PYRAZOLIN-4,5-DIONES, NOVEL PYRAZOLIN-4,5-DIONES, PREPARATION METHODS THEREFOR AND USES THEREOF

The present invention relates to novel cosmetic compositions, in particular for colouring the skin and/or the hair, these compositions comprising, in a cosmetically acceptable support, at least one 4,5-pyrazolinedione.

The invention also relates to novel 4,5-pyrazolinediones, to processes for their preparation and to their use in the cosmetics field, in particular for colouring the skin and more particularly in order to give the skin a tanned appearance.

It is known that dihydroxyacetone, or DHA, is a particularly advantageous product commonly used in cosmetics as an agent for artificially tanning the skin; when applied to the skin, in particular to the face, it affords a tanning or browning effect which is very similar in appearance to that which can result from prolonged exposure to the sun (a natural tan) or under a UV lamp. Such a use also has the advantage of entirely avoiding the risks of skin reaction generally associated with the above mentioned prolonged exposures (erythema, burning, loss of elasticity, appearance of wrinkles, premature ageing of the skin, and the like).

However, the use of DHA has certain drawbacks.

For instance, although the colour produced on the skin by applying a composition containing DHA is very close to that obtained in a natural tan, certain users may still consider it to be too yellow.

Other drawbacks also appear during the storage of compositions containing DHA. Thus, DHA has an annoying tendency, which may be more or less pronounced depending on the nature of the medium in which it is formulated, to degrade over time, this degradation generally leading in the long term to an undesirable yellowing of the compositions containing it. It also occurs that over time such compositions have a nauseating odour. Lastly, the pH of compositions containing DHA decreases over time, making them in the long run incompatible with use by topical application. These various phenomena have the effect of greatly reducing the activity of DHA, and in particular its ability to colour the skin, when these compositions are applied to the skin.

Moreover, the intensity of the coloration obtained on the skin, and especially the speed with which this coloration develops, are often considered to be insufficient by users of DHA-based self-tanning products, since the time required for the desired intensity to appear on the skin is generally several hours.

In order to increase the speed of appearance of the colour due to DHA, it has been sought to combine it with other substances. Thus, patent application EP-A-547,864 proposes to provide DHA in the presence of an amino acid and a silicone, the DHA and the amino acid being stored in separate compartments before they are applied to the skin. Mention may also be made of patent application WO-A-94/04130 which describes a device for supplying DHA at the same time as a primary amine, these two compounds also being stored in separate compartments.

However, these devices have the drawback of being complicated and of not giving any real improvement as regards the waiting time required in order to obtain satisfactory coloration of the skin. Lastly, in addition, they do not totally solve the problems due to the storage of compositions containing DHA.

In conclusion, it appears that DHA as an agent for artificially colouring the skin is not completely satisfactory and that there is thus a need for other agents which, preferably, do not have any of the disadvantages mentioned above.

To this end, novel compositions are now proposed containing, in a cosmetically acceptable support, at least one 4,5-pyrazolinedione. The time required to develop the colour after these compositions are applied to the skin is remarkably short. These compositions also have excellent stability and give the skin a colour very close to that present in a natural tan. Lastly, the staying power of the coloration on the skin is also noteworthy.

Moreover, these compositions find an advantageous application in dyeing hair.

A first subject of the invention is thus a novel composition comprising, in a cosmetically acceptable support, at least one 4,5-pyrazolinedione corresponding to formula (I) below:

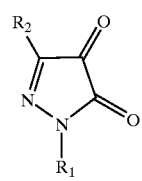

in which $R_1$ is chosen from:

a hydrogen atom; a linear or branched $C_1$–$C_{18}$ alkyl radical optionally substituted with a hydroxyl (OH), sulphonyl ($SO_3H$), carboxyl (COOH) or $C_2$–$C_4$ hydroxyalkyl radical; a cyclohexyl or cyclopentyl radical;

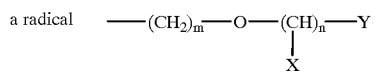

in which m is equal to 1, 2 or 3, n is equal to 1, 2 or 3, X is a hydrogen atom or a methyl radical, and Y is a methyl, hydroxyl or linear or branched $C_1$–$C_5$ alkoxy radical;

a radical —$(CH_2)_p$—OR' in which R' represents a substituted or unsubstituted phenyl or naphthyl radical and p is equal to 1 or 2;

a radical —$(CH_2)_q$—R" in which q is equal to 1, 2 or 3 and R" is chosen from:

a phenyl radical which is unsubstituted or substituted with not more than 2 radicals chosen from methyl, trifluoromethyl, methoxy and sulphonyl radicals;

a naphthyl radical, a thienyl radical, a furyl radical, a pyridyl radical or a piperidyl radical;

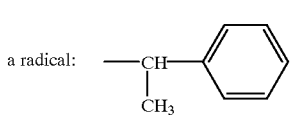

a radical: 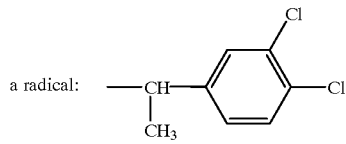

a phenyl radical; a phenyl radical substituted with a nitro radical; a phenyl radical substituted with one to three radicals chosen from: —COOH, —CH$_2$COOH, —Cl, —Br, —F, —OH, —SO$_3$H, —CH$_2$OH, —OCF$_3$, —CF$_3$, —SO$_2$CH$_3$, —SO$_2$NH$_2$, —SO$_2$NHC$_2$H$_5$, —SO$_2$NHCH$_2$CH$_2$OH, —CON(CH$_3$)$_2$, —CON(C$_2$H$_5$)$_2$, —CH$_2$N(CH$_3$)$_2$, —CH$_2$N(C$_2$H$_5$)$_2$, —NHCOCH$_3$, —NHCOC$_2$H$_5$, a C$_1$–C$_8$ alkyl radical or a radical —ZR$_3$ in which z is an oxygen or sulphur atom and R$_3$ is a hydrogen atom or a linear or branched C$_1$–C$_{18}$ alkyl radical;

a naphthyl radical optionally substituted with an —SO$_3$H radical;

a benzyl radical; a benzyl radical substituted with a —COOH, —OCH$_3$ or —SO$_3$H radical;

a pyridyl radical, a pyrimidinyl radical, a pyrazinyl radical, a triazinyl radical, a benzotriazolyl radical, a benzimidazolyl radical, a thienyl radical, an imidazolyl radical, a thiazolyl radical, a 1,2,4-triazolyl radical, an indazolyl radical, an indolyl radical, a quinolyl radical or an isoquinolyl radical;

and R$_2$ is chosen from:

a hydrogen atom; a linear or branched C$_1$–C$_6$ alkyl radical; a C$_1$–C$_4$ hydroxy alkyl radical; a methoxymethyl radical;

a phenyl radical; a phenyl radical substituted with a halogen atom, a nitro radical or a trifluoromethyl radical; a phenyl radical substituted with not more than three radicals chosen from C$_1$–C$_4$ alkyl, C$_1$–C$_4$ alkoxy, C–C$_4$ dialkylamino and C$_1$–C$_2$ alkylthio radicals;

a benzyl radical; a benzyl radical substituted with a halogen atom, a C$_1$–C$_4$ alkyl radical, a C$_1$–C$_4$ alkoxy radical, a trifluoromethyl radical or a C$_1$–C$_4$ dialkylamino radical;

a radical —(CH$_2$)$_r$—R$_4$ in which r is equal to 1, 2 or 3 and R$_4$ is chosen from:
an —SO$_3$H radical, a C$_1$–C$_2$ alkylthio radical or a benzylthio radical;
a methoxycarbonyl or ethoxycarbonyl radical;
a phenyl radical;
a C$_1$–C$_4$ alkoxy radical or a phenoxy radical optionally substituted with one or more halogen atoms;
a C$_1$–C$_4$ alkoxy radical; a trifluoromethyl radical; an acetamido radical; a C$_1$–C$_4$ dialkylamino radical; a carboxyl radical; a methoxycarbonyl radical; an ethoxycarbonyl radical;
a thienyl radical, a furyl radical, a pyridyl radical or a pyrazolyl radical.

In a preferred embodiment of the invention, these compositions are intended to artificially tan the skin.

These novel compositions have the advantage of giving the skin a tan which is very close to a natural tan, and doing so in an extremely short time. Indeed, a few minutes are sufficient to obtain a tanned complexion.

The subject of the present invention is also a cosmetic treatment process for the skin which is intended to artificially tan and/or brown it, this process consisting in applying an effective amount of a cosmetic composition in accordance with the invention or a 4,5-pyrazolinedione as mentioned above to the skin.

The subject of the present invention is also the use of a 4,5-pyrazolinedione as mentioned above in, or for the manufacture of, compositions intended to artificially tan and/or brown the skin.

In another embodiment of the invention, these cosmetic compositions are intended to dye the hair.

The subject of the present invention is thus also a cosmetic treatment process for the hair intended to dye it, this process consisting in applying an effective amount of a composition in accordance with the invention or a 4,5-pyrazolinedione as mentioned above to the hair.

The subject of the present invention is also the use of a 4,5-pyrazolinedione as mentioned above in, or for the manufacture of, compositions intended to dye the hair.

Other characteristics, aspects and advantages of the present invention will become apparent on reading the detailed description which follows.

Among the 4,5-pyrazolinediones defined above, the ones more particularly preferred are those for which R$_1$ is chosen from:

a hydrogen atom; a linear or branched C$_1$–C$_8$ alkyl radical;

a radical —(CH$_2$)$_2$—OR' in which R' represents a phenyl or naphthyl radical;

a radical —(CH$_2$)$_q$—R'' in which q is equal to 1 or 2 and R'' represents a phenyl radical optionally substituted with a trifluoromethyl radical;

a phenyl radical optionally substituted with a nitro radical, a —Cl radical, a C$_1$–C$_4$ alkyl radical or a C$_1$–C$_4$ alkoxy radical;

and those for which R$_2$ is chosen from:

a hydrogen atom; a linear or branched C$_1$–C$_4$ alkyl radical; a C$_1$–C$_4$ hydroxyalkyl radical; a methoxymethyl radical;

a phenyl radical optionally substituted with a halogen atom, a nitro radical, a C$_1$–C$_4$ alkyl radical or a C$_1$–C$_4$ alkoxy radical;

a C$_1$–C$_4$ alkoxy radical; a trifluoromethyl radical; an acetamido radical; a C$_1$–C$_4$ dialkylamino radical; a carboxyl radical; a methoxycarbonyl radical; an ethoxycarbonyl radical;

a thienyl radical, a furyl radical, a pyridyl radical or a pyrazolyl radical, the above conditions for the choice of R$_1$ and R$_2$ preferably being cumulative.

Thus, among the 4,5-pyrazolinediones which can be used in the compositions in accordance with the invention, mention may be made in particular of:

3-methyl-1-phenyl-4,5-pyrazolinedione; 1-phenyl-4,5-pyrazolinedione; 3-tert-butyl-1-phenyl-4,5-pyrazolinedione; 1,3-diphenyl-4,5-pyrazolinedione; 1-phenyl-3-(4'-methylphenyl)-4,5-pyrazolinedione; 1-phenyl-3-(3'-methoxymethyl)-4,5-pyrazolinedione; 1-phenyl-3-(4'-methoxyphenyl)-4,5-pyrazolinedione; 1-phenyl-3-(4'-nitrophenyl)-4,5-pyrazolinedione; 3-methoxy-1-phenyl-4,5-pyrazolinedione; 3-ethoxy-1-phenyl-4,5-pyrazolinedione; 3-acetamido-1-phenyl-4,5-pyrazolinedione; 3-dimethylamino-1-phenyl-4,5-pyrazolinedione; 3-diethylamino-1-phenyl-4,5-pyrazolinedione; 3-carboxy-1-phenyl-4,5-pyrazolinedione; 3-methoxycarbonyl-1-phenyl-4,5-pyrazolinedione; 3-ethoxycarbonyl-1-phenyl-4,5-pyrazolinedione;

1-[(3'-trifluoromethyl)benzyl]-3-methyl-4,5-pyrazolinedione; 1-[(1'-phenyl)ethyl]-3-methyl-4,5-pyrazolinedione; 3-methyl-4,5-pyrazolinedione; 1,3-dimethyl-4,5-pyrazolinedione; 1-(2'-phenoxy)ethyl-3-methyl-4,5-pyrazolinedione; 1-(2'-naphthyloxy)ethyl-3-propyl-4,5-pyrazolinedione; 1-(2'-naphthyloxy)ethyl-3-hydroxymethyl-4,5-pyrazolinedione; 3-tert-butyl-1-(2'-phenoxy)ethyl-4,5-pyrazolinedione; 3-methoxymethyl-1-(2'-naphthyloxy)ethyl-4,5-pyrazolinedione; 3-methyl-1-(4'-nitrophenyl)-4,5-pyrazolinedione; 3-methoxy-4,5-pyrazolinedione; 3-ethoxy-4,5-pyrazolinedione;

1-methyl-4,5-pyrazolinedione; 1-methyl-3-phenyl-4,5-pyrazolinedione; 1-methyl-3-(4'-chlorophenyl)-4,5-pyrazolinedione; 1-methyl-3-(3'-methoxyphenyl)-4,5-pyrazolinedione; 1-methyl-3-(4'-methoxyphenyl)-4,5-pyrazolinedione; 1-methyl-3-(3'-nitrophenyl)-4,5-pyrazolinedione; 1-methyl-3-(4'-methylphenyl)-4,5-pyrazolinedione; 1-methyl-3-(2'-furyl)-4,5-pyrazolinedione; 1-methyl-3-(2'-thienyl)-4,5-pyrazolinedione; 1-methyl-3-(5'-pyrazolyl)-4,5-pyrazolinedione; 1-methyl-3-(4'-pyridyl)-4,5-pyrazolinedione; 1-methyl-3-methoxy-4,5-pyrazolinedione; 3-ethoxy-1-methyl-4,5-pyrazolinedione; 3-dimethylamino-1-methyl-4,5-pyrazolinedione; 3-diethylamino-1-methyl-4,5-pyrazolinedione; 3-acetamido-1-methyl-4,5-pyrazolinedione; 3-carboxy-1-methyl-4,5-pyrazolinedione; 3-methoxycarbonyl-1-methyl-4,5-pyrazolinedione; 3-ethoxycarbonyl-1-methyl-4,5-pyrazolinedione;

1-ethyl-4,5-pyrazolinedione; 1-ethyl-3-methyl-4,5-pyrazolinedione; 1-ethyl-3-phenyl-4,5-pyrazolinedione; 1-ethyl-3-(4'-chlorophenyl)-4,5-pyrazolinedione; 1-ethyl-3-(3'-methoxyphenyl)-4,5-pyrazolinedione; 1-ethyl-3-(4'-methoxyphenyl)-4,5-pyrazolinedione; 1-ethyl-3-(3'-nitrophenyl)-4,5-pyrazolinedione; 1-ethyl-3-(4'-methylphenyl)-4,5-pyrazolinedione; 1-ethyl-3-(2'-furyl)-4,5-pyrazolinedione; 1-ethyl-3-(2'-thienyl)-4,5-pyrazolinedione; 1-ethyl-3-(5'-pyrazolyl)-4,5-pyrazolinedione; 1-ethyl-3-methoxy-4,5-pyrazolinedione; 1-ethyl-3-ethoxy-4,5-pyrazolinedione; 1-ethyl-3-dimethylamino-4,5-pyrazolinedione; 1-ethyl-3-diethylamino-4,5-pyrazolinedione; 1-ethyl-3-acetamido-4,5-pyrazolinedione; 1-ethyl-3-carboxy-4,5-pyrazolinedione; 1-ethyl-3-methoxycarbonyl-4,5-pyrazolinedione; 1-ethyl-3-ethoxycarbonyl-4,5-pyrazolinedione;

1-isopropyl-4,5-pyrazolinedione; 1-isopropyl-3-methyl-4,5-pyrazolinedione; 1-isopropyl-3-phenyl-4,5-pyrazolinedione; 1-isopropyl-3-(4'-chlorophenyl)-4,5-pyrazolinedione; 1-isopropyl-3-(3'-methoxyphenyl)-4,5-pyrazolinedione; 1-isopropyl-3-(4'-methoxyphenyl)-4,5-pyrazolinedione; 1-isopropyl-3-(3'-nitrophenyl)-4,5-pyrazolinedione; 1-isopropyl-3-(4'-methylphenyl)-4,5-pyrazolinedione; 1-isopropyl-3-(2 '-furyl)-4,5-pyrazolinedione; 1-isopropyl-3-(2'-thienyl)-4,5-pyrazolinedione; 1-isopropyl-3-(5'-pyrazolyl)-4,5-pyrazolinedione; 1-isopropyl-3-methoxy-4,5-pyrazolinedione; 1-isopropyl-3-ethoxy-4,5-pyrazolinedione; 1-isopropyl-3-dimethylamino-4,5-pyrazolinedione; 1-isopropyl-3-diethylamino-4,5-pyrazolinedione; 1-isopropyl-3-acetamido-4,5-pyrazolinedione; 1-isopropyl-3-carboxy-4,5-pyrazolinedione; 1-isopropyl-3-methoxycarbonyl-4,5-pyrazolinedione; 1-isopropyl-3-ethoxycarbonyl-4,5-pyrazolinedione;

1-tert-butyl-4,5-pyrazolinedione; 1-tert-butyl-3-methyl-4,5-pyrazolinedione; 1-tert-butyl-3-phenyl-4,5-pyrazolinedione; 1-tert-butyl-3-(4'-chlorophenyl)-4,5-pyrazolinedione; 1-tert-butyl-3-(3'-methoxyphenyl)-4,5-pyrazolinedione; 1-tert-butyl-3-(4'-methoxyphenyl)-4,5-pyrazolinedione; 1-tert-butyl-3-(3'-nitrophenyl)-4,5-pyrazolinedione; 1-tert-butyl-3-(4'-methylphenyl)-4,5-pyrazolinedione; 1-tert-butyl-3-(2'-furyl)-4,5-pyrazolinedione; 1-tert-butyl-3-(2'-thienyl)-4,5-pyrazolinedione; 1-tert-butyl-3-(5'-pyrazolyl)-4,5-pyrazolinedione; 1-tert-butyl-3-methoxy-4,5-pyrazolinedione; 1-tert-butyl-3-ethoxy-4,5-pyrazolinedione; 1-tert-butyl-3-dimethylamino-4,5-pyrazolinedione: 1-tert-butyl-3-diethylamino-4,5-pyrazolinedione; 1-tert-butyl-3-acetamido-4,5-pyrazolinedione; 1-tert-butyl-3-carboxy-4,5-pyrazolinedione; 1-tert-butyl-3-methoxycarbonyl-4,5-pyrazolinedione; 1-tert-butyl-3-ethoxycarbonyl-4,5-pyrazolinedione;

1-octyl-4,5-pyrazolinedione; 1-octyl -3-methyl-4,5-pyrazolinedione; 1-octyl-3-phenyl-4,5-pyrazolinedione; 1-octyl-3-(4'-chlorophenyl)-4,5-pyrazolinedione; 1-octyl-3-(3'-methoxyphenyl)-4,5-pyrazolinedione; 1-octyl-3-(4'-methoxyphenyl)-4,5-pyrazolinedione; 1-octyl-3-(3'-nitrophenyl)-4,5-pyrazolinedione;

1-(4'-methylphenyl)-4,5-pyrazolinedione; 1-(4'-methylphenyl)-3-methyl-4,5-pyrazolinedione; 1-(4'-methylphenyl)-3-phenyl-4,5-pyrazolinedione; 1-(4'-methylphenyl)-3-(4'-chlorophenyl)-4,5-pyrazolinedione; 1-(4'-methylphenyl)-3-(3'-methoxyphenyl)-4,5-pyrazolinedione; 1-(4'-methylphenyl)-3-(4'-methoxyphenyl)-4,5-pyrazolinedione; 1-(4'-methylphenyl)-3-(3'-nitrophenyl)-4,5-pyrazolinedione; 1-(4'-methylphenyl)-3-(4'-methylphenyl)-4,5-pyrazolinedione; 1-(4'-methylphenyl)-3-(2'-furyl)-4,5-pyrazolinedione; 1-(4'-methylphenyl)-3-(2'-thienyl)-4,5-pyrazolinedione; 1-(4'-methylphenyl)-3-(5'-pyrazolyl)-4,5-pyrazolinedione; 1-(4'-methylphenyl)-3-methoxy-4,5-pyrazolinedione; 1-(4'-methylphenyl)-3-ethoxy-4,5-pyrazolinedione; 1-(4'-methylphenyl)-3-dimethylamino-4,5-pyrazolinedione; 1-(4-methylphenyl)-3-diethylamino-4,5-pyrazolinedione; 1-(4'-methylphenyl)-3-acetamido-4,5-pyrazolinedione; 1-(4'-methylphenyl)-3-carboxy-4,5-pyrazolinedione; 1-(4'-methylphenyl)-3-methoxycarbonyl-4,5-pyrazolinedione; 1-(4'-methylphenyl)-3-ethoxycarbonyl-4,5-pyrazolinedione;

1-benzyl-4,5-pyrazolinedione; 1-benzyl-3-methyl-4,5-pyrazolinedione; 1-benzyl-3-phenyl-4,5-pyrazolinedione; 1-benzyl-3-(4'-methylphenyl)-4,5-pyrazolinedione; 1-benzyl-3-(3'-methoxyphenyl)-4,5-pyrazolinedione; 1-benzyl-3-(4'-methoxyphenyl)-4,5-pyrazolinedione; 1-benzyl-3-(3'-nitrophenyl)-4,5-pyrazolinedione;

1-(4'-methoxyphenyl)-4,5-pyrazolinedione; 1-(4'-methoxyphenyl)-3-methyl-4,5-pyrazolinedione; 1-(4'-methoxyphenyl) -3-(3'-methoxyphenyl)-4,5-pyrazolinedione; 1-(4'-methoxyphenyl)-3-phenyl-4,5-pyrazolinedione; 1-(4'-methoxyphenyl)-3-(4'-chlorophenyl)-4,5-pyrazolinedione; 1-(4'-methoxyphenyl)-3-(4'-methoxyphenyl)-4,5-pyrazolinedione; 1-(4'-methoxyphenyl)-3-(3'-nitrophenyl)-4,5-pyrazolinedione; 1-(4'-methoxyphenyl)-3-methoxy-4,5-pyrazolinedione; 1-(4'-methoxyphenyl)-3-ethoxy-4,5-pyrazolinedione; 1-(4'-methoxyphenyl)-3-dimethylamino-4,5-pyrazolinedione; 1-(4'-methoxyphenyl)-3-diethylamino-4,5-pyrazolinedione; 1-(4'-methoxyphenyl)-3-acetamido4,5-pyrazolinedione; 1-(4'-methoxyphenyl)-3-carboxy-4,5-pyrazolinedione; 1-(4'-methoxyphenyl)-3-methoxycarbonyl-4,5-pyrazolinedione; 1-(4'-methoxyphenyl)-3-ethoxycarbonyl-4,5-pyrazolinedione;

1-(4'-chlorophenyl)-4,5-pyrazolinedione; 1-(4'-chlorophenyl)-3-methyl-4,5-pyrazolinedione; 1-(4'-chlorophenyl)-3-phenyl-4,5-pyrazolinedione; 1-(4'-chlorophenyl)-3-(4'-methylphenyl)-4,5-pyrazolinedione; 1-(4'-chlorophenyl)-3-(3'-methoxyphenyl)-4,5-pyrazolinedione; 1-(4'-chlorophenyl)-3-(4'-methoxyphenyl)-4,5-pyrazolinedione; 1-(4'-chlorophenyl)-3-(3'-nitrophenyl)-4,5-pyrazolinedione; 1-(4'-chlorophenyl)-3-methoxy-4,5-pyrazolinedione;

1-(4'-chlorophenyl)-3-ethoxy-4,5-pyrazolinedione; 1-(4'-chlorophenyl)-3-dimethylamino-4,5-pyrazolinedione; 1-(4'-chlorophenyl)-3-diethylamino-4,5-pyrazolinedione; 1-(4'-chlorophenyl)-3-acetamido-4,5-pyrazolinedione; 1-(4'-chlorophenyl)-3-carboxy-4,5-pyrazolinedione; 1-(4'-chlorophenyl)-3-methoxycarbonyl-4,5-pyrazolinedione; 1-(4'-chlorophenyl)-3-ethoxycarbonyl-4,5-pyrazolinedione;

1-(4'-nitrophenyl)-4,5-pyrazolinedione; 1-(4'-nitrophenyl)-3-methyl-4,5-pyrazolinedione; 1-(4'-nitrophenyl)-3-phenyl-4,5-pyrazolinedione; 1-(4'-nitrophenyl)-3-(4'-methylphenyl)-4,5-pyrazolinedione; 1-(4'-nitrophenyl)-3-(3'-methoxyphenyl)-4,5-pyrazolinedione; 1-(4'-nitrophenyl)-3-(4'-methoxyphenyl)-4,5-pyrazolinedione; 1-(4'-nitrophenyl)-3-(3'-nitrophenyl)-4,5-pyrazolinedione;

1-phenyl-3-trifluoromethyl-4,5-pyrazolinedione; 1-methyl-3-trifluoromethyl-4,5-pyrazolinedione; 1-isopropyl-3-trifluoromethyl4,5-pyrazolinedione; 1-ethyl-3-trifluoromethyl-4,5-pyrazolinedione; 3-trifluoromethyl-4,5-pyrazolinedione;

Among the 4,5-pyrazolinediones which can be used in the context of the present invention, the ones most particularly preferred are those for which, cumulatively, $R_1$ is chosen from:

hydrogen and methyl, ethyl, isopropyl, tert-butyl and phenyl radicals; and $R_2$ is chosen from:

hydrogen and methyl, phenyl, methoxyphenyl, methoxy, ethoxy, carboxyl, methoxycarbonyl, ethoxycarbonyl, acetamido, dimethylamino, diethylamino, trifluoromethyl, furyl and pyridyl radicals.

Thus, in the compositions according to the invention, it is most particularly preferred to use 3-methyl-1-phenyl-4,5-pyrazolinedione; 3-methyl-4,5-pyrazolinedione; 1,3-dimethyl-4,5-pyrazolinedione; 1-ethyl-3-methyl-4,5-pyrazolinedione; 1-isopropyl-3-methyl-4,5-pyrazolinedione; 1-tert-butyl-3-methyl-4,5-pyrazolinedione; 1-methyl-3-phenyl-4,5-pyrazolinedione; 1-methyl-3-(3'-methoxyphenyl)-4,5-pyrazolinedione; 3-(2'-furyl)-1-methyl-4,5-pyrazolinedione; 1-methyl-3-(4'-pyridyl)-4,5-pyrazolinedione; 1-methyl-3-methoxy-4,5-pyrazolinedione; 3-ethoxy-1-methyl-4,5-pyrazolinedione; 3-dimethylamino-1-methyl-4,5-pyrazolinedione; 3-diethylamino-1-methyl-4,5-pyrazolinedione; 3-acetamido-1-methyl-4,5-pyrazolinedione; 1-phenyl-4,5-pyrazolinedione; 1-methyl-4,5-pyrazolinedione; 1-ethyl-4,5-pyrazolinedione; 1-isopropyl-4,5-pyrazolinedione; 1-tert-butyl-4,5-pyrazolinedione; 3-methoxy-1-phenyl-4,5-pyrazolinedione; 3-ethoxy-1-phenyl-4,5-pyrazolinedione; 3-acetamido-1-phenyl-4,5-pyrazolinedione; 3-dimethylamino-1-phenyl-4,5-pyrazolinedione; 3-diethylamino-1-phenyl-4,5-pyrazolinedione; 1-phenyl-3-trifluoromethyl-4,5-pyrazolinedione; 1-methyl-3-trifluoromethyl-4,5-pyrazolinedione; 1-isopropyl-3-trifluoromethyl-4,5-pyrazolinedione; 1-ethyl-3-trifluoromethyl-4,5-pyrazolinedione; 3-trifluoromethyl-4,5-pyrazolinedione; 3-carboxy-1-phenyl-4,5-pyrazolinedione; 3-methoxycarbonyl-1-phenyl-4,5-pyrazolinedione; 3-ethoxycarbonyl-1-phenyl-4,5-pyrazolinedione; 3-methoxy-4,5-pyrazolinedione; 3-ethoxy-4,5-pyrazolinedione; 3-carboxy-1-methyl-4,5-pyrazolinedione; 3-methoxycarbonyl-1-methyl-4,5-pyrazolinedione; 3-ethoxycarbonyl-1-methyl-4,5-pyrazolinedione.

The 4,5-pyrazolinedione(s) is(are) used in an effective amount to give a coloration either on the skin or on the hair, depending on the case. Thus, they are generally present in the compositions according to the invention at a concentration of between 0.05 and 10% by weight, preferably between 0.05 and 5% by weight, relative to the total weight of the composition.

When the compositions according to the invention are intended to artificially tan the skin, the pH can range between 3 and 10. It is preferably between 3 and 7.

When the compositions according to the invention are intended to dye the hair, the pH can range between 2 and 8. It is preferably between 2 and 6.

The vehicle (or the cosmetically acceptable support) for the compositions according to the invention is preferably water, alone or with one or more organic solvents or fatty substances.

The solvents which can be used are preferably chosen from alcohols such as ethyl alcohol and cetyl alcohol, or alternatively from propylene glycol, ethylene glycol monoethyl ether and ethylene glycol monobutyl ether.

As fatty substance, mention may be made of oils and waxes of mineral, animal or plant origin.

The term oil is understood to refer to a compound which is liquid at room temperature. The term wax is understood to refer to a compound which is solid or substantially solid at room temperature, and whose melting point is generally greater than 35° C.

As oils, mention may be made of mineral oils (petroleum jelly); plant oils (sweet almond oil, macadamia oil, grapeseed oil); synthetic oils such as perhydrosqualene, fatty alcohols, acids or esters (octyl palmitate, isopropyl lanolate, triglycerides, including those of capric/caprylic acids), oxyethylenated or oxypropylenated fatty esters and ethers; silicone oils (cyclomethicone, polydimethylsiloxanes or PDMSs) or fluoro oils, and polyalkylenes.

As waxy compounds, mention may be made of jojoba oil, paraffin, carnauba wax, beeswax and hydrogenated castor oil.

The other constituents which can form part of the formulation of the compositions towards which the invention is directed, in particular thickeners, emulsifiers and gelling agents, are those which are used conventionally in the cosmetics and/or dermatological field.

As emulsifiers, mention may be made of fatty acid esters of polyethylene glycol (PEG), fatty acid esters of glycerol (glyceryl stearate) or fatty acid esters of a sugar (sorbitan stearate), as well as the polyoxyethylenated or polyoxypropylenated derivatives thereof, cyclomethicones and dimethicone copolyols, anionic surfactants (potassium or sodium alkyl phosphate) and polyalkoxylated fatty alcohols.

Polyalkoxylated fatty alcohols such as oxypropylenated butyl alcohols, oxyethylenated caprylic alcohols and oxyethylenated cetyl alcohols are preferably used.

Thickeners which may be used are crosslinked polyacrylic acids, modified or unmodified guar gums and cellulose gums such as hydroxypropyl guar gum, methylhydroxyethylcellulose, hydroxypropylmethylcellulose or hydroxyethylcellulose.

Gelling agents which may be mentioned are modified clays (bentones), metal salts of fatty acids (aluminium stearate), ethylene/acrylate copolymers, silicas, polyethylenes, calcium silicates or ethylcellulose.

The compositions according to the invention can also contain any other cosmetically or dermatologically acceptable constituent usually used in compositions of this type, such as softeners, antioxidants, opacifiers, stabilizers, emollients, insect repellents, organic sunscreens which are active in the UV-A and/or UV-B range, photoprotective inorganic pigments and nanopigments, moisturizers, vitamins, fragrances, preserving agents, fillers, sequestering agents, dyes, and in particular compounds known for their self-tanning action such as, for example, dihydroxyacetone, methylglyoxal, glyceraldehyde, erythrulose, alloxan, 2,3-dihydroxysuccinic dialdehyde, 2-amino-3-hydroxysuccinic dialdehyde and 2-benzylamino-3-hydroxysuccinic dialdehyde.

Needless to say, a person skilled in the art will take care to select this or these optional complementary compound(s) and/or the amounts thereof such that the advantageous properties intrinsically associated with the composition in accordance with the invention are not, or are not substantially, adversely affected by the addition(s) envisaged.

This composition can be in particular in the form of a simple or complex emulsion (O/W, W/O, O/W/O or W/O/W emulsion) such as a cream, a milk, a gel or a cream-gel, a powder or a solid tube and can optionally be packaged as an aerosol and can be in the form of a mousse or a spray.

Preferably, this composition is in the form of an oil-in-water emulsion.

The compositions with which the invention is concerned can be prepared according to techniques which are well known to those skilled in the art, in particular those techniques intended for the preparation of emulsions of oil-in-water or water-in-oil type.

The subject of the present invention is also novel 4,5-pyrazolinediones corresponding to the general formula (I') below:

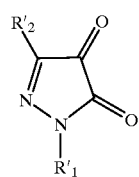

(I')

in which $R'_1$ and $R'_2$ have the same meanings as those given above for $R_1$ and $R_2$ in formula (I) with, however, the following provisos:
(i) when $R'_1$ represents a phenyl radical, then $R'_2$ is other than a hydrogen atom, a methyl radical, a tert-butyl radical, a phenyl radical, a p-methylphenyl radical, a p-nitrophenyl radical or a p-methoxyphenyl radical,
(ii) when $R'_2$ represents a methyl radical, $R'_1$ is other than a p-nitrophenyl radical, a 2-phenoxyethyl radical, a 2-naphthyloxyethyl radical, a methyl radical, an m-trifluoromethylbenzyl radical, a 1-phenylethyl radical, a 1-cyclohexylethyl radical or a 1-(3',4'-dichlorophenyl)ethyl radical,
(iii) when $R'_1$ represents a 2-naphthyloxyethyl radical, $R'_2$ is other than an n-propyl radical or a hydroxymethyl radical,
(iv) when $R'_1$ represents a 2-phenoxyethyl radical, $R'_2$ is other than a tert-butyl radical,
(v) when $R'_2$ represents a methoxymethyl radical, $R'_1$ is other than a 2-naphthyloxyethyl radical or a 1-(3',4'-dichlorophenyl)ethyl radical,
(vi) when $R'_1$ represents a hydrogen atom, $R'_2$ is other than a methyl radical.

Among the 4,5-pyrazolinediones defined above, mention may be made more particularly of those for which $R'^1$ is chosen from:
a hydrogen atom; a linear or branched $C_1$–$C_8$ alkyl radical;
a radical —$(CH_2)_2$—OR' in which R' represents a phenyl or naphthyl radical;
a radical —$(CH_2)_q$—R" in which q is equal to 1 or 2 and R" represents a phenyl radical optionally substituted with a trifluoromethyl radical;
a phenyl radical optionally substituted with a nitro radical, a —Cl radical, a $C_1$–$C_4$ alkyl radical or a $C_1$–$C_4$ alkoxy radical,
and those for which $R'_2$ is chosen from:
a hydrogen atom; a linear or branched $C_1$–$C_4$ alkyl radical; a $C_1$–$C_4$ hydroxyalkyl radical; a methoxymethyl radical;
a phenyl radical optionally substituted with a halogen atom, a nitro radical, a $C_1$–$C_4$ alkyl radical or a $C_1$–$C_4$ alkoxy radical;
a $C_1$–$C_4$ alkoxy radical; a trifluoromethyl radical; an acetamido radical; a $C_1$–$C_4$ dialkylamino radical; a carboxyl radical; a methoxycarbonyl radical; an ethoxycarbonyl radical;
a thienyl radical, a furyl radical, a pyridyl radical or a pyrazolyl radical,
with the provisos (i) to (vi) defined above, the above conditions for the choice of $R'_1$ and $R'_2$ preferably being cumulative.

Among the novel compounds of formula (I'), mention may thus be made most particularly of those for which $R'_1$ is chosen from:
hydrogen and methyl, ethyl, isopropyl, tert-butyl and phenyl radicals;
and $R'_2$ is chosen from:
hydrogen and methyl, phenyl, methoxyphenyl, methoxy, ethoxy, carboxyl, methoxycarbonyl, ethoxycarbonyl, acetamido, dimethylamino, diethylamino, trifluoromethyl, furyl and pyridyl radicals, with the provisos (i) to (vi) defined above.

Thus, mention may be made in particular of:
1-ethyl-3-methyl-4,5-pyrazolinedione; 1-isopropyl-3-methyl-4,5-pyrazolinedione; 1-tert-butyl-3-methyl-4,5-pyrazolinedione; 1-methyl-3-phenyl-4,5-pyrazolinedione; 1-methyl-3-(3'-methoxyphenyl)-4,5-pyrazolinedione; 3-(2'-furyl)-1-methyl-4,5-pyrazolinedione; 1-methyl-3-(4'-pyridyl)-4,5-pyrazolinedione; 1-methyl-3-methoxy-4,5-pyrazolinedione; 3-ethoxy-1-methyl-4,5-pyrazolinedione; 3-dimethylamino-1-methyl-4,5-pyrazolinedione; 3-diethylamino-1-methyl-4,5-pyrazolinedione; 3-acetamido-1-methyl-4,5-pyrazolinedione; 1-methyl-4,5-pyrazolined-one; 1-ethyl-4,5-pyrazolinedione; 1-isopropyl-4,5-pyrazolinedione; 1-tert--butyl-4,5-pyrazolinedione; 3-methoxy-1-phenyl-4,5-pyrazolinedione; 3-ethoxy-1-phenyl-4,5-pyrazolinedione; 3-acetamido-1-phenyl-4,5-pyrazolinedione; 3-dimethylamino-1-phenyl-4,5-pyrazolinedione; 3-diethylamino-1-phenyl-4,5-pyrazolinedione; 1-phenyl-3-trifluoromethyl-4,5-pyrazolinedione; 1-methyl-3-trifluoromethyl-4,5-pyrazolinedione; 1-isopropyl-3-trifluoromethyl-4,5-pyrazolinedione; 1-ethyl-3-trifluoromethyl-4,5- pyrazolinedione; 3-trifluoromethyl-4,5-pyrazolinedione; 3-carboxy-1-phenyl-4,5-pyrazolinedione; 3-methoxycarbonyl-1-phenyl-4,5-pyrazolinedione; 3-ethoxycarbonyl-1-phenyl-4,5-pyrazolinedione; 3-methoxy-4,5-pyrazolinedione; 3-ethoxy-4,5-pyrazolinedione; 3-carboxy-1-methyl-4,5-pyrazolinedione; 3-methoxycarbonyl-1-methyl-4,5-pyrazolinedione; 3-ethoxycarbonyl-1-methyl-4,5-pyrazolinedione.

The subject of the invention is also a process for the preparation of the novel compounds of formula (I'), this process being characterized in that it comprises the following steps (the meanings of R'$_1$ and R'$_2$ are as given above):
  i) a 5-pyrazolinone (1) is reacted with an aromatic nitroso compound (2) in order to obtain the corresponding 4-arylimino-5-pyrazolinone (3):

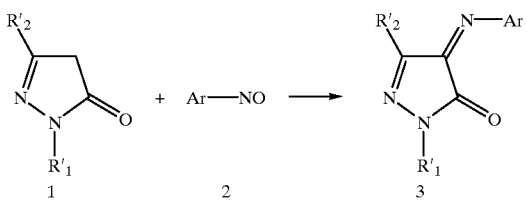

this reaction preferably being carried out in a lower alcohol such as methanol, ethanol or isopropanol, at a temperature of between 65° C. and 85° C., at the reflux point of the solvent used, and preferably in the presence of a catalytic amount of a weak base of carbonate or bicarbonate type, ii) the 4-arylimino-5-pyrazolinone (3) is then hydrolysed, preferably in strong acid medium, in order to obtain the corresponding 4,5-pyrazolinedione derivative of formula (I'):

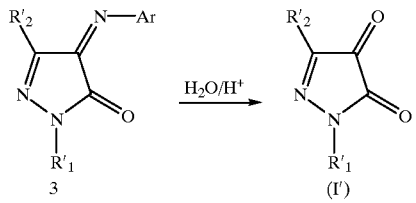

In such a process, the aromatic nitroso derivative from the first step is preferably a p-nitrosodialkylaniline of formula (2)':

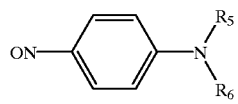

in which R$_5$ and R$_6$ represent a linear or branched C$_1$–C$_4$ alkyl radical.

The acid hydrolysis in the second step of the preparation process according to the invention is preferably carried out with dilute sulphuric acid or aqueous hydrochloric acid at room temperature in the presence of a co-solvent for the 4,5-pyrazolinedione, which is immiscible with water, thereby making it possible advantageously to extract the compound as it forms, making it easier to isolate in very high purity. The water-immiscible co-solvent can be a haloge-nated solvent such as, for example, dichloromethane or 1,2-dichloroethane. In a preferred embodiment of the invention, the water-immiscible co-solvent is an ether such as diethyl ether or diisopropyl ether.

The subject of the invention is also a second process for the preparation of the novel compounds of formula (I'), this process being characterized in that it comprises the following steps (the meanings of R'$_1$ and R'$_2$ are as given above):
  i) bromine is reacted with a 5-pyrazolinone of formula (1) in order to obtain the corresponding 4,4-dibromo-5-pyrazolinone of formula (4) (step a),
  ii) lead diacetate is then reacted so as to form the corresponding diacetate of formula (5), this product being an unstable intermediate which leads spontaneously, by elimination of acetic anhydride, to the desired 4,5-pyrazolinedione derivative of formula (I') (step b), these two steps a and b thus being carried out according to the following reaction scheme:

Step a

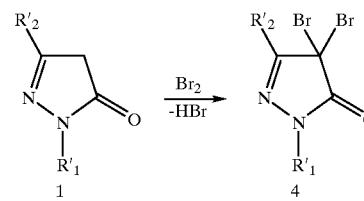

Step b

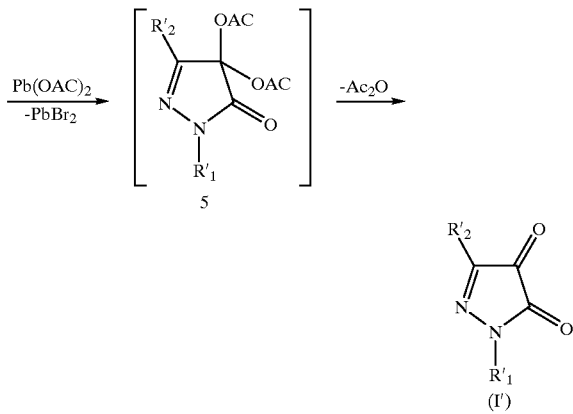

The first step of dibromination is preferably carried out in aqueous medium in the presence of two equivalents of bromine at room temperature. The reaction is generally complete within a few hours: the dibromo derivative precipitates as it is formed, thereby allowing an isolation by simple filtration in high purity.

The second step is advantageously carried out at the reflux point of acetic acid in a few hours, and the lead dibromide which forms can be separated out very easily by simple filtration.

Concrete, but in no way limiting, examples intended to illustrate the invention will now be given.

EXAMPLE 1

The coloration obtained using formulations containing 3-methyl-1-phenyl-2-pyrazoline-4,5-dione, on the one hand, and dihydroxyacetone (DHA), on the other hand, were studied by means of a comparative in vivo test.

Three formulations A, B and C were thus prepared, the compositions of which are collated in Table (I) below (the amounts are expressed by weight relative to the total weight of the composition):

TABLE (I)

| Composition (% by weight) | Formulation A (invention) | Formulation B (comparative) | Formulation C (comparative) |
|---|---|---|---|
| 3-methyl-1-phenyl-2-pyrazolin-4,5-dione | 1 | 0 | 0 |
| Dihydroxyacetone | 0 | 1 | 5 |
| Excipient* qsp | 100 | 1000 | 100 |

(*)The excipient is a mixture of water/ethanol/1,2-propanediol in a 1/2/1 weight ratio.

Evaluation Protocol

The colorations obtained with the formulations described above were evaluated by means of an in vivo test on three volunteers according to the following method: the formulations A, B and C were applied to the skin on delimited 2.5×2.5 cm areas on the forearms of the three individuals. The intensity of coloration associated with each of the formulations was then determined after a certain time T, i.e. $\Delta L_T$. To do this, colorimetric measurements were taken using a Minolta CM 1000 calorimeter. A first measurement was taken just before the products were applied ($T_0$), a second 30 minutes after applying the products ($T_{30\ min}$) and a final measurement 5 hours after applying the products ($T_{5h}$).

The results are expressed in the system (L, a, b) in which L represents the luminance, a represents the red-green axis (−a=green, +a=red) and b represents the yellow-blue axis (−b=blue, +b=yellow).

To evaluate the intensity of the coloration, the value of interest is $\Delta L$ ($\Delta L = L_T - L_{T0}$) which quantifies the darkness of the colour: the more negative the value of $\Delta L$, the darker the colour.

The results (average values of $\Delta L$ obtained 30 min and 5 h after application) are given in Table (II) below:

TABLE (II)

| | Formulation Time | A (invention) | B (comparative) | C (comparative) |
|---|---|---|---|---|
| ΔL | T = 30 min | −4.3 | −0.1 | −0.7 |
| | T = 5 h | −8.2 | −2.2 | −5.3 |

Composition A containing 3-methyl-1-phenyl-2-pyrazoline-4,5-dione according to the invention leads to a skin coloration which appears more quickly and is of stronger intensity than that of compositions B and C containing DHA (for an equal content of B or 5 times as much of C as of the 3-methyl-1-phenyl-2-pyrazoline-4,5-dione).

EXAMPLE 2

A concrete example of a self-tanning oil-in-water emulsion in accordance with the invention is given below:

| Phase A: | |
|---|---|
| - 80/20 mixture of cetylstearyl alcohol and of oxyethylenated (33 EO) cetylstearyl alcohol, sold under the name "Dehsconet 390" by the company Tensia | 7% |

-continued

| Phase A: | |
|---|---|
| - mixture of glyceryl mono- and distearate sold under the name "Cerasynth SD" by the company ISP | 2% |
| - cetyl alcohol | 1.5% |
| - polydimethylsiloxane sold under the name "DC200 Fluid" by the company Dow Corning | 1.5% |
| - $C_{12}/C_{15}$ alkyl benzoate sold under the name "Finsolv TN" by the company Finetex | 15% |
| - 3-methyl-1-phenyl-2-pyrazoline-4,5-dione | 1% |

| Phase B: | |
|---|---|
| - glycerol | 20% |
| - preserving agents | qs |
| - demineralized water | qs 100% |

This emulsion was prepared according to the following procedure: Phases A and B were brought to 80° C. separately. Phase A was then poured into Phase B with stirring using a Moritz stirrer. The mixture was then homogenized, after which it was allowed to cool to room temperature.

EXAMPLE 3

Concrete examples of compositions in accordance with the invention for dyeing the hair are given here:

| Composition 1: | |
|---|---|
| - 3-methyl-1-phenyl-4,5-pyrazolinedione | 0.113 g |
| - benzyl alcohol | 2 g |
| - $C_{16}$—$C_{18}$ fatty alcohol | 1.8 g |
| - sodium ether sulphate of $C_{16}$—$C_{18}$ fatty alcohol | 1.8 g |
| - water | 14 g |

The pH of the composition was adjusted to a value of 2.6 with 10% hydrochloric acid.

This composition was applied for 30 minutes to locks of natural grey hair containing 90% white hairs and to locks of permanent-waved grey hair containing 90% white hairs, at a rate of 2 to 5 g/g of hair. The composition was applied either at room temperature (20° C.) or at 50° C.

The locks were then rinsed, either thoroughly with tap water or using a standard shampoo. They were then dried for 10 minutes, either with a hair-dryer or under a dryer hood, at a temperature of between 60 and 65° C.

The intensity of coloration of the locks was then determined. The results are given in the system (L, a, b) in which L represents the luminance, a represents the red-green axis (−a=green, +a=red) and b represents the yellow-blue axis (−b=blue, +b=yellow).

The higher the value of a, the redder the lock.

The results for the hair before treatment (untreated) and after treatment with composition 1 in accordance with the invention (treated) are collated in Table (III) below:

TABLE (III)

| | Natural grey hair containing 90% white hairs | | | Permanent-waved grey hair containing 90% white hairs | | |
|---|---|---|---|---|---|---|
| | Untreated | Treated (temperature) | | Untreated | Treated (temperature) | |
| | | 20° C. | 50° C. | | 20° C. | 50° C. |
| L | 55.1 | 41.5 | 35.5 | 52.5 | 30 | 31.4 |
| a | 0.4 | 13.8 | 17.9 | 0.3 | 21.1 | 21.3 |
| b | 15 | 7.1 | 6.2 | 12.8 | 3.2 | 5.3 |

These results show clearly that the locks were dyed a strong red colour.

| Composition 2: | |
|---|---|
| - 3-methyl-1-phenyl-4,5-pyrazolinedione | 0.113 g |
| - benzyl alcohol | 2 g |
| - $C_{16}$–$C_{18}$ fatty alcohol | 1.8 g |
| - sodium ether sulphate of $C_{16}$–$C_{18}$ fatty alcohol | 1.8 g |
| - water | 14 g |

The pH of the composition was adjusted to a value of 5.8 with triethanolamine.

This composition was applied for 30 minutes to locks of hair of the same nature as above (natural grey hair containing 90% white hairs and permanent-waved grey hair containing 90% white hairs), at a rate of 2 to 5 g/g, at a temperature of 37° C.

The locks were then rinsed and dried as above. The intensity of their coloration was also measured as above.

The results for the hair before treatment (untreated) and after treatment with composition 2 in accordance with the invention (treated) are collated in Table (IV) below:

Table (IV)

| | Natural grey hair containing 90% white hairs | | Permanent-waved grey hair containing 90% white hairs | |
|---|---|---|---|---|
| | Untreated | Treated 37° C. | Untreated | Treated 37° C. |
| L | 55.1 | 34.6 | 52.6 | 28.4 |
| a | 0.4 | 19.9 | 0.3 | 21 |
| b | 15 | 4.7 | 12.8 | 3.7 |

These results show clearly that the locks were dyed a strong red colour.

What is claimed is:

1. A composition comprising, in a cosmetically acceptable support, at least one 4,5-pyrazolinedione corresponding to formula (I):

$$\text{(I)}$$

[Structure: pyrazolinedione with $R_2$ at position 3, $R_1$ on N1]

wherein
$R_1$ is:
a hydrogen atom; a linear or branched $C_1$–$C_{18}$ alkyl radical, unsubstituted or substituted with a hydroxyl (OH), sulphonyl ($SO_3H$), carboxyl (COOH) or $C_2$–$C_4$ hydroxyalkyl radical; a cyclohexyl radical; cyclopentyl radical;

a radical —$(CH_2)_m$—O—$(CH)_n$—Y with X branching wherein
m is 1, 2 or 3,
n is 1, 2 or 3,
X is a hydrogen atom or a methyl radical, and
Y is methyl, hydroxyl or a linear or branched $C_1$–$C_5$ alkoxy radical;
a radical —$(CH_2)_p$—OR' wherein R' represents a substituted or unsubstituted phenyl or naphthyl radical and p is 1 or 2;
a radical —$(CH_2)_q$—R" in which q is 1, 2 or 3 and R" is a phenyl radical, unsubstituted or substituted with not more than 2 radicals which are each independently methyl, trifluoromethlyl, methoxy, or sulphonyl;
a naphthyl radical, a thienyl radical, a furyl radical, a pyridyl radical; or a piperidyl radical;

a radical: —CH($CH_3$)—phenyl a radical: —CH($CH_3$)—cyclohexyl a radical: —CH($CH_3$)—(2,4-dichlorophenyl)

a phenyl radical; a phenyl radical substituted with a nitro radical; a phenyl radical substituted with from one to three radicals which are each independently: —COOH, —$CH_2COOH$, —Cl, —Br, —F, —OH, —$SO_3H$, —$CH_2OH$, —$OCF_3$, —$CF_3$, —$SO_2CH_3$, —$SO_2NH_2$, —$SO_2NHC_2H_5$, —$SO_2NHCH_2CH_2OH$, —$CON(CH_3)_2$, —$CON(C_2H_5)_2$, —$CH_2N(CH_3)_2$, —$CH_2N(C_2H_5)_2$, —$NHCOCH_3$, —$NHCOC_2H_5$, a $C_1$–$C_8$ alkyl radical; or a radical —$ZR_3$, wherein Z is an oxygen or sulphur atom and $R_3$ is a hydrogen atom or a linear or branched $C_1$–$C_{18}$ alkyl radical;
a naphthyl radical, unsubstituted or substituted with an —$SO_3H$ radical;

a benzyl radical; or a benzyl radical substituted with a —COOH, —OCH$_3$ or —SO$_3$H radical;

a pyridyl radical, a pyrimidinyl radical, a pyrazinyl radical, a triazinyl radical, a benzotriazolyl radical, a benzimidazolyl radical, a thienyl radical, an imidazolyl radical, a thiazolyl radical, a 1,2,4-triazolyl radical, an indazolyl radical, an indolyl radical, a quinolyl radical, or an isoquinolyl radical; and R$_2$ is:

a hydrogen atom; a linear or branched C$_1$–C$_6$ alkyl radical; a C$_1$–C$_4$ hydroxyalkyl radical; or a methoxymethyl radical;

a phenyl radical; a phenyl radical substituted with a halogen atom, a nitro radical; a trifluoromethyl radical; or a phenyl radical substituted with not more than three radicals which are each independently C$_1$–C$_4$ alkyl, C$_1$–C$_4$ alkoxy, C$_1$–C$_4$ dialkylamino, or C$_1$–C$_2$ alkylthio;

a benzyl radical; a benzyl radical substituted with a halogen atom, a C$_1$–C$_4$ alkyl radical, a C$_1$–C$_4$ alkoxy radical, a trifluoromethyl radical; or a C$_1$–C$_4$ dialkylamino radical;

a radical —(CH$_2$)$_r$—R$_4$ wherein r is 1, 2 or 3 and R$_4$ is an —SO$_3$H radical, a C$_1$–C$_2$ alkylthio radical; a benzylthio radical; a methoxycarbonyl radical; ethoxycarbonyl radical; a phenyl radical; a C$_1$–C$_4$ alkoxy radical; or a phenoxy radical, unsubstituted or substituted with at least one halogen atoms;

a C$_1$–C$_4$ alkoxy radical; a trifluoromethyl radical; an acetamido radical; a C$_1$–C$_4$ dialkylamino radical; a carboxyl radical; a methoxycarbonyl radical; or an ethoxycarbonyl radical;

a thienyl radical, a furyl radical, a pyridyl radical, or a pyrazolyl radical.

2. A composition according to claim 1, wherein R$_1$ is:

a hydrogen atom; a linear or branched C$_1$–C$_8$ alkyl radical;

a radical —(CH$_2$)$_2$—OR' wherein R' represents a phenyl or naphthyl radical;

a radical —(CH$_2$)$_q$—R" wherein q is 1 or 2 and R" represents a phenyl radical, unsubstituted or substituted with a trifluoromethyl radical; or a phenyl radical, unsubstituted or substituted with a nitro radical, a —Cl radical, a C$_1$–C$_4$ alkyl radical, or a C$_1$–C$_4$ alkoxy radical.

3. A composition according to claim 1, wherein R$_2$ is a hydrogen atom; a linear or branched C$_1$–C$_4$ alkyl radical; a C$_1$–C$_4$ hydroxyalkyl radical; a methoxymethyl radical;

a phenyl radical, unsubstituted or substituted with a halogen atom, a nitro radical, a C$_1$–C$_4$ alkyl radical, or a C$_1$–C$_4$ alkoxy radical;

a C$_1$–C$_4$ alkoxy radical; a trifluoromethyl radical; an acetamido radical; a C$_1$–C$_4$ dialkylamino radical; a carboxyl radical; a methoxycarbonyl radical; an ethoxycarbonyl radical;

a thienyl radical; a furyl radical; a pyridyl radical; or a pyrazolyl radical.

4. A composition according to claim 1, wherein

R$_1$ is hydrogen, methyl, ethyl, isopropyl, tert-butyl, or phenyl; and

R$_2$ is hydrogen, methyl, phenyl, methoxyphenyl, methoxy, ethoxy, carboxyl, methoxycarbonyl, ethoxycarbonyl, acetamido, dimethylamino, diethylamino, trifluoromethyl, furyl, or pyridyl.

5. A composition according to claim 4, wherein said at least one 4,5-pyrazolinedione is:

3-methyl-1-phenyl-4,5-pyrazolinedione;
3-methyl-4,5-pyrazolinedione;
1,3-dimethyl-4,5-pyrazolinedione;
1-ethyl-3-methyl-4,5-pyrazolinedione;
1-isopropyl-3-methyl-4,5-pyrazolinedione;
1-tert-butyl-3-methyl4,5-pyrazolinedione;
1-methyl-3-phenyl4,5-pyrazolinedione;
1methyl-3-(3'-methoxyphenyl)-4,5-pyrazolinedione;
3-(2'-furyl)-1-methyl-4,5-pyrazolinedione;
1-methyl-3-(4'-pyridyl)-4,5-pyrazolinedione;
1-methyl-3-methoxy-4,5-pyrazolinedione;
3-ethoxy-1-methyl-4,5-pyrazolinedione;
3-dimethylamino-1-methyl-4,5-pyrazolinedione;
3-diethylamino-1-methyl-4,5-pyrazolinedione;
3-acetamido-1-methyl-4,5-pyrazolinedione;
1-phenyl-4,5-pyrazolinedione;
1-methyl-4,5-pyrazolinedione;
1-ethyl-4,5-pyrazolinedione;
1-isopropyl-4,5-pyrazolinedione;
1-tert-butyl-4,5-pyrazolinedione;
3-methoxy-1-phenyl-4,5-pyrazolinedione;
3-ethoxy-1-phenyl-4,5-pyrazolinedione;
3-acetamido-1-phenyl-4,5-pyrazolinedione;
3-dimethylamino-1-phenyl-4,5-pyrazolinedione;
3-diethylamino-1-phenyl-4,5-pyrazolinedione;
1-phenyl-3-trifluoromethyl-4,5-pyrazolinedione;
1-methyl-3-trifluoromethyl-4,5-pyrazolinedione;
1-isopropyl-3-trifluoromethyl-4,5-pyrazolinedione;
1-ethyl-3-trifluoromethyl-4,5-pyrazolinedione;
3-trifluoromethyl-4,5-pyrazolinedione;
3-carboxy-1-phenyl-4,5-pyrazolinedione;
3-methoxycarbonyl-1-phenyl-4,5-pyrazolinedione;
3-ethoxycarbonyl-1-phenyl-4,5-pyrazolinedione;
3-methoxy-4,5-pyrazolinedione;
3-ethoxy-4,5-pyrazolinedione;
3-carboxy-1-methyl-4,5-pyrazolinedione;
3-methoxycarbonyl-1-methyl-4,5-pyrazolinedione; or
3-ethoxycarbonyl-1-methyl-4,5-pyrazolinedione.

6. A composition according to claim 1, wherein said at least one 4,5-pyrazolinedione is present in an amount ranging from 0.05 to 10% by weight relative to the total weight of said composition.

7. A composition according to claim 6, wherein said at least one 4,5-pyrazolinedione is present in an amount ranging from 0.05 to 5% by weight relative to the total weight of said composition.

8. A composition according to claim 1, wherein said cosmetically acceptable support comprises water, an organic solvent, or a fatty substance, or a mixture thereof.

9. A composition according to claim 1, wherein said composition further comprises a thickener, an emulsifier, or a gelling agent.

10. A composition according to claim 1, wherein said composition is in the form of a simple or complex emulsion, a powder, a solid tube, a mousse, or a spray.

11. A process for artificially tanning or browning skin comprising applying an effective amount for tanning or browning of a 4,5-pyrazolinedione compound according to claim 1 or composition comprising said compound according to claim 1 to said skin.

12. A process for dyeing hair comprising applying an effective amount for dyeing of a 4,5-pyrazolinedione compound according to claim 1 or a composition comprising said compound according to claim 1 to said hair.

* * * * *

UNITED STATES PATENT AND TRADEMARK OFFICE
CERTIFICATE OF CORRECTION

PATENT NO. : 6,322,775 B1
DATED : November 27, 2001
INVENTOR(S) : Malle et al.

It is certified that error appears in the above-identified patent and that said Letters Patent is hereby corrected as shown below:

Column 16, claim 1,
Line 34, "trifluoromethlyl" should read -- trifluoromethyl --.

Column 17, claim 1,
Line 24, "alkythio" should read -- alkylthio --.

Column 18, claim 5,
Line 9, "1-tert-butyl-3-methyl4, 5-pyrazolinedione" should read -- 1-tert-butyl-3-methyl-4,5-pyrazolinedione --.

Column 18, claim 5,
Line 11, "1 methyl-3-(3'-methoxyphenyl)-4,5-pyrazolinedione" should read -- 1-methyl-3-(3'methoxyphenyl)-4,5-pyrazolinedione --.

Signed and Sealed this

Nineteenth Day of March, 2002

JAMES E. ROGAN
*Director of the United States Patent and Trademark Office*

*Attest:*

*Attesting Officer*